(12) United States Patent
Thompson et al.

(10) Patent No.: US 6,670,446 B1
(45) Date of Patent: Dec. 30, 2003

(54) N¹ MODIFIED GLYCOPEPTIDES

(75) Inventors: Richard Craig Thompson, Frankfort, IN (US); Stephen Charles Wilkie, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/647,113

(22) PCT Filed: Feb. 26, 1999

(86) PCT No.: PCT/US99/04306
§ 371 (c)(1),
(2), (4) Date: Sep. 26, 2000

(87) PCT Pub. No.: WO99/56760
PCT Pub. Date: Nov. 11, 1999

Related U.S. Application Data

(60) Provisional application No. 60/083,879, filed on May 1, 1998.

(51) Int. Cl.⁷ .................................................. C07K 7/50
(52) U.S. Cl. ............................ 530/317; 514/8; 514/11; 530/322
(58) Field of Search ...................... 514/11, 8; 530/317, 530/322

(56) References Cited

U.S. PATENT DOCUMENTS

| | | |
|---|---|---|
| 4,639,433 A | 1/1987 | Hunt et al. ................... 514/8 |
| 4,643,987 A | 2/1987 | Nagarajan et al. ............. 514/8 |
| 4,698,327 A | 10/1987 | Nagarajan et al. ............. 514/8 |
| 5,312,738 A | 5/1994 | Hamill et al. ................. 435/75 |
| 5,534,420 A | 7/1996 | Debono et al. ............. 435/71.3 |
| 5,591,714 A | 1/1997 | Nagarajan et al. ............. 514/9 |

FOREIGN PATENT DOCUMENTS

| | | |
|---|---|---|
| EP | 435503 A1 | 7/1991 |
| EP | 435503 B1 | 7/1991 |
| EP | 667353 A1 | 8/1995 |

OTHER PUBLICATIONS

Allen, N. et al., "Hexapeptide Derivatives of Glycopeptide Antibiotics: Tools for Mechanism of Action Studies," *Antimicrobial Agents and Chemotherapy*, vol. 46, No. 8, pp. 2344–2348 (Aug. 2002).

Harris, C. et al., "The Role of the Chlorine Substituents in the Antibiotic Vancomycin: Preparation and Characterization of Mono– and Didechlorovancomycin," *J. Am. Chem. Soc.*, vol. 107, pp. 6652–6658 (1985).

Kannan, R. et al., "Function of the Amino Sugar and N–Terminal Amino Acid of the Antibiotic Vancomycin in Its Complexation with Cell Wall Peptides," *J. Am. Chem. Soc.*, vol. 110, pp. 2946–2953 (1988).

Mackay, J. et al., "Glycopeptide Antibiotic Activity and the Possible Role of Dimerization: A Model for Biological Signaling," *J. Am. Chem. Soc.*, vol. 116, pp. 4581–4590 (1994).

Walsh, C.T. et al., "Bacterial Resistance to Vancomycin: Five Genes and One Missing Hydrogen Bond Tell the Story," *Chemistry & Biology*, vol. 3, No. 1, pp. 21–28 (Jan. 1996).

Nagarajan, J. Antibiotics, 1993, 46, 1181–1195.

Nagarajan, Schabel, J. Chem. Soc., Chem. Commun. 1988, 1306–1307.

Booth, et al., J. Chem. Soc., Chem. Commun. 1987, 1694–1695.

Zmijewski, et al., J. Natural Products 1989, 52, 203–206.

Cristofaro, et al., J. Antibiotics 1995, 48, 805–810.

Miroshnikova, et al., J. Antibiotics 1996, 49, 1157–1161.

Gorlitzer, et al., J. Chem. Soc., Perkins Trans. 1 1999, 3253–3257.

Nicas, et al., Antimicrobial Agents and Chemotherapy, 1989, 33(9): 1477–1481.

*Primary Examiner*—Christopher S. F. Low
*Assistant Examiner*—David Lukton
(74) *Attorney, Agent, or Firm*—Merchant & Gould P.C.

(57) ABSTRACT

Described herein are N'-acylated derivatives of desleucylA82846B. The compounds are useful as antibacterial agents.

8 Claims, No Drawings

$N^1$ MODIFIED GLYCOPEPTIDES

This application is a 371 of PCT/US99/04306, filed Feb. 26, 1999, which claims priority to provisional application No. 60/083,879, filed May. 1, 1998.

The present invention is directed to glycopeptides and is directed in particular to modifications of A82846B and its $N^{DISACC}$ variations. In the claimed compounds, the original $N^1$ amino acid, N-methyl-D-leucine, has been removed and replaced with an acyl group or with an acyl group derived from an alternate α-amino acid.

The present invention is directed to compounds of the formula

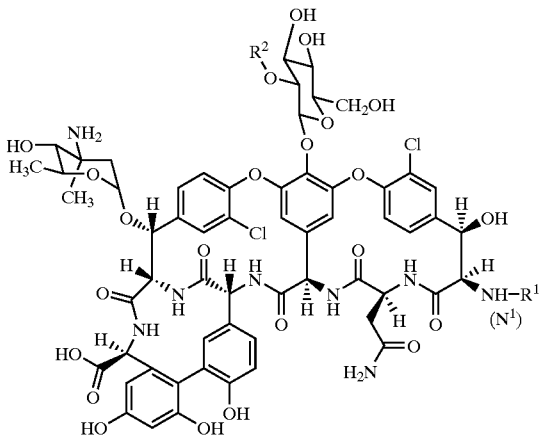

I where in $R^1$ represents
  alkanoyl of $C_2$–$C_{10}$ which is unsubstituted, or which is substituted by a phenyl, or which is substituted on other than the α-carbon atom by an amino or protected amino group;
  benzoyl or substituted benzoyl bearing one or two substituents each of which is independently halo, loweralkyl of $C_1$–$C_4$, loweralkoxy of $C_1$–$C_4$ or phenyl;
  an acyl derived from an α-amino acid or an acyl derived from a protected α-amino acid, said α-amino acid being selected from the group consisting of:
    alanine,
    arginine,
    asparagine,
    aspartic acid,
    cysteine,
    glutamic acid,
    glutamine,
    glycine,
    histidine,
    isoleucine,
    leucine,
    lysine,
    methionine,
    3-phenylalanine,
    3-(p-chlorophenyl) alanine,
    proline,
    serine,
    threonine,
    tryptophan and valine,
  in either D- or L-form; or
    an acyl derived from an α-amino acid as defined above which bears on the amine a substituent which is alkyl of $C_1$–$C_{10}$, benzyl, phenylbenzyl, or p-chlorobenzyl, with the proviso that the acyl derived from N-methyl-D-leucine is excluded;
  $R^2$ represents hydrogen, or epivancosaminyl of the formula

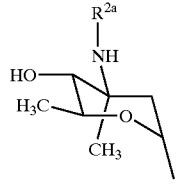

wherein $R^{2a}$ represents hydrogen or —$CH_2$—$R^3$; and $R^3$ represents hydrogen, alkyl of $C_1$–$C_{11}$, alkyl of $C_1$–$C_{11}$-$R^4$, or $R^4$-(linker$_{(0\ or\ 1)}$-$R^4$)$_{o\ or\ 1}$,
  wherein each $R^4$ is independently phenyl or phenyl substituted by one or two substituents, each of which is independently halo, loweralkyl of $C_1$–$C_8$, loweralkoxy of $C_1$–$C_8$, loweralkylthio of $C_1$–$C_4$, or trifluoromethyl, and "linker" is —O—, —$CH_2$—, or —O—($CH_2$)$_n$— wherein n is 1–3; and the pharmaceutically acceptable salts thereof.

When $R^1$ represents alkanoyl of $C_2$–$C_{10}$, it can be a straight-chain alkanoyl, or it can be an alkanoyl which is branched to any degree. Likewise, when $R^3$ represents alkyl of $C_1$–$C_{11}$, it can be straight-chain or branched.

The compounds of the present invention are prepared from the corresponding "A82846B hexapeptides" of the formula:

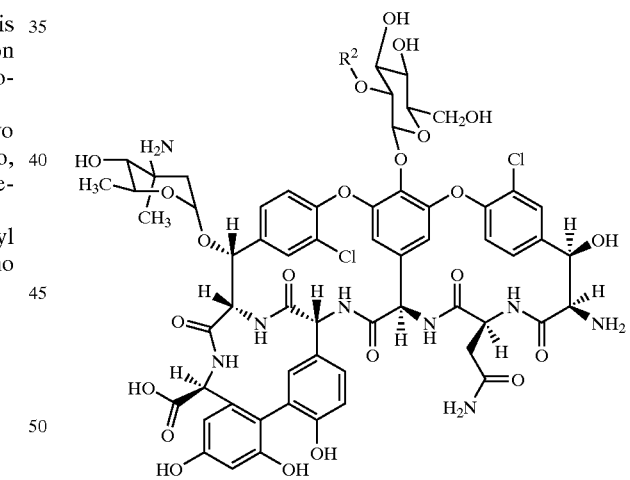

II wherein $R^2$ is as defined above. These "A82846B hexapeptides" are so called because the normal $N^1$ amino acid N-methyl-D-leucine, has been removed, reducing the number of amino acids in the parent glycopeptide from seven to six.

The compounds of the present invention are prepared by reacting an A82846B hexapeptide with an activated ester of an alkanoic acid of the desired acyl group $R^1$. By "activated ester" is meant an ester which renders the carboxyl function more reactive to coupling with the amine of the A82846B hexapeptide. The reaction of the A82846B hexapeptide and activated ester is carried out in an organic solvent, suitably a polar solvent such as dimethylformamide, dimethyl sulfoxide, or a mixture of dimethylformamide and dimethyl sulfoxide. The reaction proceeds under temperatures of a wide range, such as 250 to 100° C., but is preferably carried out at temperatures of about 25 to 35° C. Some of the desired product is produced shortly upon contacting the reactants, but higher yields are obtained with reaction times of from about 1 to about 24 hours, oftentimes from about 1 to about 5 hours. Isolation and purification are carried out under conventional procedures.

The starting A82846B hexapeptides are themselves synthesized from the parent glycopeptides:

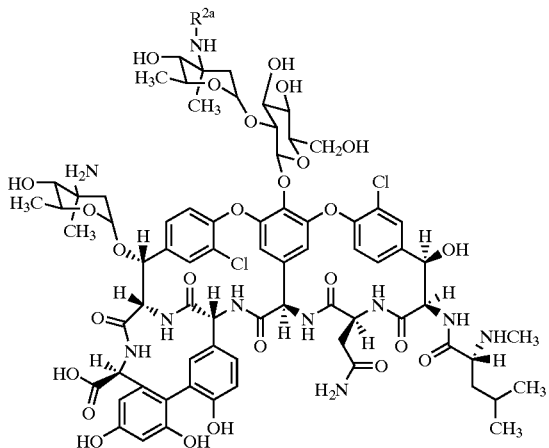

wherein $R^{2a}$ is as defined above. This synthesis is by the "Edman degradation", a two-step process for the cleavage of the N-terminal residue of a peptide or protein. The above parent glycopeptide is first reacted with an isothiocyanate of the formula SCN-$R^5$, to obtain an intermediate $N^{LEU}$-(thiocarbamoyl)-A82846B compound of the formula

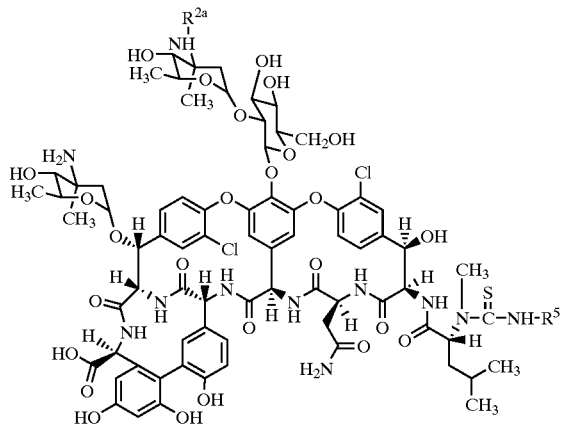

In the foregoing formula, $R^5$ represents alkyl of $C_1$–$C_{10}$, phenyl, naphthyl, or phenyl substituted by one or two substituents, each of which is independently halo, loweralkyl of $C_1$–$C_4$, loweralkoxy of $C_1$–$C_4$, benzyloxy, nitro, or

wherein each $R^6$ is independently loweralkyl of $C_1$–$C_4$.

This reaction is conveniently carried out in water with pyridine, at a temperature of 25°–30° C., employing a slight excess of the isothiocyanate reactant. The $N^{LEU}$-(thiocarbamoyl)A82846B intermediate can be separated in conventional manner or can be employed after removal of reaction solvent in the second step of the Edman degradation.

In the second step, the $N^{LEU}$-(thiocarbamoyl)A82846B is reacted with an organic acid, preferably trifluoroacetic acid, in a non-polar solvent such a dichloromethane. The reaction proceeds at temperatures of from 0° C. to 35° C. but is preferably carried out at temperatures of from 0° C. to 25° C. The reaction is generally complete in several hours. The resulting hexapeptide product is separated and purified if desired in conventional procedures.

The second step of the Edman degradation can in some instances result in loss of the disaccharide epivancosamine. Longer reaction times can be used to obtain the desepivancosaminyl compound ($R^2$=hydrogen).

Other variations at the disaccharide position of the molecule can be obtained in conventional procedures. As described above, the Edman degradation and subsequent acylation can be carried out with the naturally-occurring disaccharide ($R^2$=epivancosaminyl with $R^{2a}$=H) or with a disaccharide derivative ($R^2$=epivancosaminyl with $R^{2a}$=$CH_2$—$R^3$). This approach to synthesis of the present compounds is illustrated by the preparations below of Examples 12 and 26. However, it is also possible to prepare those claimed compounds with a disaccharide derivative ($R^2$=epivancosaminyl with $R^{2a}$=—$CH_2$—$R^3$) by first conducting the Edman degradation and subsequent acylation on A82846B, with its naturally occurring $R^2$=epivancosaminyl, and thereafter introducing the desired epivancosaminyl substituent —$CH_2$—$R^3$. This is illustrated by Examples 34 and 35.

Whether the —$CH_2$—$R^3$ substituent is introduced prior to Edman degradation and acylation, or after, the same conventional process is used. In this process, the substrate compound is reductively alkylated with the aldehyde suitable to introduce the desired —$CH_2$—$R^3$ group. This process is taught in various references, see U.S. Pat. No. 5,591,714, and EPO 667,353.

The compounds of the present invention readily form salts, which can be prepared in conventional manner.

The following examples illustrate the preparation of the compounds of the present invention.

Preparation of $N^{LEU}$-(Phenylthiocarbamoyl)-$N^{DISACC}$-(p-(p-chlorophenyl)benzyl)A82846B $N^{DISACC}$-(p-(p-Chlorophenyl)benzyl)A82846B trihydrochloride (100.0 mg, 0.0526 mmol) was dissolved in 10 ml $H_2O$-pyridine (1:1 v/v) and treated with phenyl isothiocyanate (0.010 ml, 0.083 mmol). The resulting mixture was stirred at room temperature for 1 hr at which time HPLC analysis indicated complete consumption of the starting material. The reaction mixture was concentrated in vacuo and the crude product was purified by preparative HPLC to give 76.6 mg (76% yield) of the title compound. FAB-MS: calc. for $C_{93}H_{102}Cl_3N_{11}O_{26}S$ 1925.5, obtained 1928.5 (M+3).

Preparation of $N^{DISACC}$-(p-(p-Chlorophenyl) benzyl)-desleucylA82846B from Isolated Thiourea A sample of the purified $N^{LEU}$-(phenylthiocarbamoyl)-$N^{DISACC}$-(p-(p-chlorophenyl)benzyl)A82846B (63.3 mg, 0.0327 mmol) was suspended in 10 ml $CH_2Cl_2$, cooled to 0° C., then treated with trifluoroacetic acid (0.10 ml). After 1 hr the reaction mixture was warmed to room temperature and stirred an additional 2 hr. The solvent was removed in vacuo and the crude product was purified by preparative HPLC to give 25.3 mg (46% yield) of the title compound as a white powder. FAB-MS: calc. for $C_{79}H_{84}Cl_3N_9O_{25}$ 1663.5, obtained 1666.4 (M+3).

Preparation of $N^{DISACC}$-(p-Phenylbenzyl) desleucylA82846B without Isolation of Thiourea Intermediate $N^{DISACC}$-(p-Phenylbenzyl)A82846B (41.0 mg, 0.0233 mmol) was dissolved in 4 ml $H_2O$-pyridine (1:1 v/v) and treated with phenyl isothiocyanate (0.0040 ml, 0.033 mmol). The resulting mixture was stirred at room temperature for 3 hr at which time HPLC analysis indicated complete consumption of the starting material. The reaction mixture was concentrated in vacuo to give the crude thiourea intermediate as a white solid. The thiourea derivative was then suspended in 10 ml $CH_2Cl_2$, cooled to 0° C., then treated with trifluoroacetic acid (0.25 ml). After 30 minutes the reaction mixture was warmed to room temperature and stirred an additional 1 hr. The solvent was removed in vacuo and the crude product was purified by preparative HPLC to give 14.0 mg (37% yield) of the title compound as a white powder. FAB-MS: calc. for $C_{79}H_{85}Cl_2N_9O_{25}$ 1629.5, obtained 1632.5 (M+3).

Preparation of Example 1

A sample of desleucylA82846B (101 mg, 0.0689 mmol) and the hydroxybenzotriazole hydrate active ester of 4-phenylbenzoic acid (47 mg, 0.149 mmol) was dissolved in 10 ml DMF. The resulting mixture was stirred at room temperature for 2 hours at which time HPLC analysis revealed complete consumption of the starting material. The reaction mixture was concentrated in vacuo and the crude product was purified by preparative HPLC to give 14 mg (12% yield) of $N^1$-(p-phenylbenzoyl)desleucylA82846B.

Preparation of Example 26

A sample of $N^{DISACC}$-(p-phenylbenzyl) desleucylA82846B (140 mg, 0.0858 mmol) and the hydroxybenzotriazole hydrate active ester of N-BOC-D-proline (66 mg, 0.199 mmol) was dissolved in 12 ml DMF. The resulting mixture was stirred at room temperature for 1 hour at which time HPLC analysis revealed consumption of the starting material. The reaction mixture was concentrated in vacuo and the crude product purified by preparative HPLC to give 77.5 mg (49% yield) of $N^1$-(N-BOC-D-proline) derivative of $N^{DISACC}$-(p-phenylbenzyl) desleucylA82846B.

Preparation of Example 12

A sample of purified $N^1$-(N-BOC-D-proline) derivative of $N^{DISACC}$-(p-phenylbenzyl)desleucylA82846B (52.5 mg, 0.0287 mmol) was suspended in 9 ml $CH_2Cl_2$, cooled to 0° C., then treated with trifluoroacetic acid (0.5 ml). After 10 minutes the reaction mixture was warmed to room tempera-ture and stirred for an additional 50 minutes. HPLC analysis revealed complete consumption of the starting material. The solvent was removed in vacuo, and the crude product was purified by preparative HPLC to give 15 mg (30% yield) of $N^1$-D-proline derivative of $N^{DISACC}$-(p-phenylbenzyl) desleucylA82846B.

Preparation of Examples 34 and 35

A sample of $N^1$-D-leucine derivative of desleucylA82846B (95 mg, 0.0602 mmol) and p-phenylbenzaldehyde (14 mg, 0.0768 mmol) was dissolved in 10 ml N,N-dimethylformamide (DMF) and 10 ml methanol (MeOH). The resulting mixture was heated to 75° C. and stirred for 1 hour 15 minutes. At this time, sodium cyanoborohydride (26 mg, 0.413 mmol) was added and the reaction stirred at 75° C. for another 1 hour 30 minutes at which time HPLC analysis revealed consumption of the starting material. The reaction mixture was concentrated in vacuo and the crude product purified by preparative HPLC to give 32 mg (30%) of $N^1$-(N-p-phenylbenzyl)-D-leucine derivative of desleucylA82846B and 3 mg (2.6%) of $N^{DISACC}$-(p-phenylbenzyl)-$N^1$-(N-p-phenylbenzyl)-D-leucine derivative of desleucylA82846B.

The HPLC procedures reported in these examples were as follows:

Analytical: Reactions were monitored by analytical HPLC using a Waters C18 μBondapak or Novapak $C_{18}$ column (3.9×300 mm) and UV detection at 280 nm. Elution was accomplished with a linear gradient of 5% $CH_3CN$-95% buffer to 80% $CH_3CN$-20% buffer over 30 minutes. The buffer used was 0.5% triethylamine in water, adjusted to pH 3 with $H_3PO_4$.

Preparative: Crude reaction mixtures were purified by preparative HPLC using a Waters $C_{18}$ Nova-Pak column (40×300 mm) and UV detection at 280 nm. Elution was accomplished with a linear gradient of 5% $CH_3CN$-95% buffer to 80% $CH_3CN$-20% buffer over 30 minutes. The buffer used was 0.5% triethylamine in water, adjusted to pH 3 with $H_3PO_4$. The desired fractions were subsequently desalted with a Waters $C_{18}$ Sep-Pak (35 cc) followed by lyophilization.

Compounds were desalted as follows. A Waters Sep-Pak cartridge was pre-wet with methanol (2–3 column volumes) then conditioned with water (2–3 column volumes). The sample, dissolved in a minimum volume of water, was loaded onto the Sep-Pak column which was then washed with water (2–3 column volumes) to remove the unwanted salts. The product was then eluted with an appropriate solvent system, typically 1:1 $CH_3CN/H_2O$, $CH_3CN$, and/or methanol. The organic solvent component was removed in vacuo and the resulting aqueous solution lyophilized to give the final product.

Representative compounds of the present invention are listed in the following tables:

TABLE I

| | | | | SIMPLE ACYL DERIVATIVES |
|---|---|---|---|---|
| Example # | FAB-MS | M + X | HPLC, min | Compound Name |
| 1 | 1644.2 | 1 | 14.7 | $N^1$-(p-phenylbenzoyl)desleucylA82846B |
| 2 | 1667.4 | 2 | 17.3 | $N^1$-(8-phenyl-n-octanoyl)desleucylA82846B |
| 3 | 1834.7 | 3 | 20.4 | $N^1$-(8-phenyl-n-octanoyl)-$N^{DISACC}$-(p-phenylbenzyl)desleucylA82846B |
| 4 | 1564.4 | 3 | 11.0 | $N^1$-(4-methyl-n-pentanoyl)desleucylA82846B |

TABLE I-continued

SIMPLE ACYL DERIVATIVES

| Example # | FAB-MS | M + X | HPLC, min | Compound Name |
|---|---|---|---|---|
| 5 | 1730.4 | 3 | 17.3 | $N^1$-(4-methyl-n-pentanoyl)-$N^{DISACC}$-(p-phenylbenzyl)desleucylA82846B |
| 6 | 1812.7 | 3 | 18.9 | $N^1$-(p-phenylbenzoyl)-$N^{DISACC}$-(p-phenylbenzyl)desleucylA82846B |
| 7 | 1764.4 | 0 | 18.7 | $N^1$-(4-methyl-n-pentanoyl)-$N^{DISACC}$-[p-(p-chlorophenyl)benzyl]desleucylA82846B |
| 8 | 1868.5 | 3 | 23.0 | $N^1$-(8-phenyl-n-octanoyl)-$N^{DISACC}$-[p-(p-chlorophenyl)benzyl]desleucylA82846B |
| 9 | 1892.9 | 2 | 21.1 | $N^1$-[7-(tert-butoxycarboxamido)-n-heptanoyl]-$N^{DISACC}$-[p-(p-chlorophenyl)benzyl]desleucylA82846B |
| 10 | 1793.5 | 3 | 14.9 | $N^1$-(7-amino-n-heptanoyl)-$N^{DISACC}$-[p-(p-chlorophenyl)benzyl]desleucylA82846B |

TABLE II

AMINO ACID DERIVATIVES

| Example # | FAB-MS | M + X | HPLC, min | Compound Name |
|---|---|---|---|---|
| 11 | 1845.5 | 3 | 18.3 | $N^1$-(N-BOC-L-leucine) derivative of $N^{DISACC}$-(p-phenylbenzyl)desleucylA82846B |
| 12 | 1729.3 | 3 | 14.2 | $N^1$-D-proline derivative of $N^{DISACC}$-(p-phenylbenzyl)desleucylA82846B |
| 13 | 1745.4 | 3 | 14.2 | $N^1$-D-leucine derivative of $N^{DISACC}$-(p-phenylbenzyl)desleucylA82846B |
| 14 | 1679.6 | 3 | 13.3 | $N^1$-(N-BOC-D-leucine) derivative of desleucylA82846B |
| 15 | 1863.3 | 3 | 18.0 | $N^1$-(N-BOC-D-methionine) derivative of $N^{DISACC}$-(p-phenylbenzyl)desleucylA82846B |
| 16 | 1794.7 | 3 | 14.9 | $N^1$-(N,N'-DIBOC-D-lysine) derivative of desleucylA82846B |
| 17 | 1579.2 | 3 | 8.5 | $N^1$-D-leucine derivative of desleucylA82846B |
| 18 | 1845.5 | 3 | 18.3 | $N^1$-(N-BOC-D-leucine) derivative of $N^{DISACC}$-(p-phenylbenzyl)desleucylA82846B |
| 19 | 1960.4 | 3 | 19.2 | $N^1$-($N^1N'$-DIBOC-D-lysine) derivative of $N^{DISACC}$-(p-phenylbenzyl)desleucylA82846B |
| 20 | 1747.2 | 3 | 15.6 | $N^1$-[N-BOC-D-3-(p-chlorophenyl)alanine] derivative of desleucylA82846B |
| 21 | 1913.5 | 3 | 19.6 | $N^1$-[N-BOC-D-3-(p-chlorophenyl)alanine] derivative of $N^{DISACC}$-(p-phenylbenzyl)desleucylA82846B |
| 22 | 1813.5 | 3 | 14.4 | $N^1$-[D-3-(p-chlorophenyl)alanine] derivative of $N^{DISACC}$-(p-phenylbenzyl)desleucylA82846B |
| 23 | 1760.4 | 3 | 12.9 | $N^1$-D-lysine derivative of $N^{DISACC}$-(p-phenylbenzyl)desleucylA82846B |
| 24 | 1663.1 | 3 | 11.6 | $N^1$-(N-BOC-D-proline) derivative of desleucylA82846B |
| 25 | 1919.3 | 4 | 18.7 | $N^1$-(N-BOC-D-tryptophan) derivative of $N^{DISACC}$-(p-phenylbenzyl)desleucylA82846B |
| 26 | 1830.1 | 3 | 17.7 | $N^1$-(N-BOC-D-proline) derivative of $N^{DISACCC}$-(p-phenylbenzyl)desleucylA82846B |
| 27 | 1745.2 | 3 | 15.1 | $N^1$-L-leucine derivative of $N^{DISACC}$-(p-phenylbenzyl)desleucylA82846B |
| 28 | 1913.4 | 3 | 19.4 | $N^1$-[N-BOC-L-3-(p-chlorophenyl)alanine] derivative of $N^{DISACC}$-(p-phenylbenzyl)desleucylA82846B |
| 29 | 1829.5 | 3 | 17.1 | $N^1$-(N-BOC-L-proline) derivative of $N^{DISACC}$-(p-phenylbenzyl)desleucylA82846B |
| 30 | 1960.5 | 3 | 19.1 | $N^1$-(N,N'-DIBOC-L-lysine) derivative of $N^{DISACC}$-(p-phenylbenzyl)desleucylA82846B |
| 31 | 1760.4 | 3 | 13.3 | $N^1$-L-lysine derivative of $N^{DISACC}$-(p-phenylbenzyl)desleucylA82846B |
| 32 | 1729.4 | 3 | 14.3 | $N^1$-L-proline derivative of $N^{DISACC}$-(p-phenylbenzyl)desleucylA82846B |
| 33 | 1813.3 | 3 | 16.2 | $N^1$-[L-3-(p-chlorophenyl)alanine] derivative of $N^{DISACC}$-(p-phenylbenzyl)desleucylA82846B |
| 34 | 1745.4 | 3 | 13.3 | $N^1$-[N-(p-phenylbenzyl)-D-leucine] derivative of desleucylA82846B |
| 35 | 1911.6 | 3 | 17.9 | $N^1$-[N-(p-phenylbenzyl)-D-leucine] derivative of $N^{DISACC}$-(p-phenylbenzyl)desleucylA82846B |
| 36 | 1536.5 | 3 | 16.5 | $N^1$-(N-BOC-D-leucine) derivative of desepivancosaminyl desleucylA82846B |
| 37 | 1436.3 | 3 | 9.1 | $N^1$-D-leucine derivative of desepivancosaminyl-desleucylA82846B |
| 38 | 1747.4 | 3 | 14.5 | $N^1$-(N-n-hexyl-D-leucine) derivative of $N^{DISACC}$-n-hexyl desleucylA82846B |
| 39 | 1661.7 | 1 | 11.0 | $N^1$-(N-n-hexyl-D-leucine) derivative of desleucylA82846B |

TABLE II-continued

AMINO ACID DERIVATIVES

| Example # | FAB-MS | M + X | HPLC, min | Compound Name |
|---|---|---|---|---|
| 40 | 1727.3 | 3 | 14.8 | $N^1$-(N-BOC-N-methyl-D-phenylalanine) derivative of desleucylA82846B |
| 41 | 1679.2 | 3 | 14.1 | $N^1$-(N-BOC-N-methyl-D-valine) derivative of desleucylA82846B |
| 42 | 1577.3 | 1 | 7.7 | $N^1$-(N-methyl-D-valine) derivative of desleucylA82846B |

The compounds of the present invention are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of the present invention. In this embodiment, the compounds can be used to control and treat infections due to various bacteria, but especially gram-positive bacteria. In a preferred embodiment, the compounds are used to control and treat infections due to bacteria resistant to existing antibacterials. For example, certain bacteria are resistant to methicillin, and yet others are resistant to vancomycin and/or teicoplanin. The present compounds provide a technique for controlling and treating infections due to such resistant bacterial species.

In carrying out this embodiment of the invention, the compounds of the present invention can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg/kg will be effective; and in many situations, lesser doses of from about 0.5 to about 50 mg/kg will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of the present invention, in combination with a pharmaceutically-acceptable carrier. Such carriers are well known for both oral and parenteral routes of delivery. In general, a formulation will comprise a compound of the present invention in a concentration of from about 0.1 to about 90% by weight, and often from about 1.0 to about 3%.

The antibacterial efficacy of the present compounds is illustrated by Table III. The minimal inhibitory concentrations (MICs) were determined using a standard broth microdilution assay.

TABLE III

ACTIVITY OF SIMPLE ACYL DERIVATIVES*

| Example # | Resistant | Sensitive | SA 446 | SA 489 | SA 447 | SA X400 | SA X778 | SA 491 | SA S13E | SA 1199 |
|---|---|---|---|---|---|---|---|---|---|---|
| 1 | >128 | 4 | 1 | 0.5 | 0.25 | 0.5 | 0.125 | 0.5 | 0.25 | 0.125 |
| 2 | >128 | 1.5 | ≤.06 | ≤.06 | ≤.06 | ≤.06 | ≤.06 | ≤.06 | ≤.06 | 0.125 |
| 3 | 6.7 | 2.6 | 1 | 1 | 1 | 1 | 1 | 1 | 2 | 1 |
| 4 | >128 | 4 | 1 | 0.5 | 1 | 0.25 | 0.5 | 0.125 | 0.5 | 0.5 |
| 5 | 27 | 0.44 | 0.125 | 0.125 | ≤.06 | ≤.06 | 0.125 | ≤.06 | 0.125 | 0.25 |
| 6 | 38 | 3.5 | 1 | 2 | 2 | 1 | 0.5 | 0.5 | 1 | 0.5 |
| 7 | 3.4 | 0.22 | 0.5 | 1 | 0.5 | 0.5 | 1 | 0.125 | 0.5 | 1 |
| 8 | 4 | 2 | 16 | 8 | 8 | 8 | 4 | 4 | 8 | 4 |
| 9 | 4.8 | 0.66 | 2 | 1 | 2 | 2 | 1 | 1 | 1 | 1 |
| 10 | 5.7 | 0.57 | | | | | | | | |

| Example # | SA 1199A | SH 105 | SH 415 | SE 270 | EF 180 | EF 180-1 | EF 2041 | EF 276 | EG 245 | HFRD | EC 14 |
|---|---|---|---|---|---|---|---|---|---|---|---|
| 1 | ≤.06 | 2 | 4 | 0.5 | 64 | 0.125 | 0.125 | 0.125 | 2 | no growth | >64 |
| 2 | ≤.06 | 1 | 8 | 0.125 | 8 | ≤.06 | ≤.06 | ≤.06 | 0.25 | no growth | >64 |
| 3 | 0.5 | 1 | 2 | 1 | 1 | ≤.06 | 0.5 | 0.5 | 2 | >64 | >64 |
| 4 | 0.5 | 0.25 | 16 | 0.5 | >64 | 0.5 | 1 | 0.5 | 4 | >64 | >64 |
| 5 | ≤.06 | ≤.06 | 1 | 0.25 | 4 | ≤.06 | ≤.06 | 1 | 0.25 | >64 | >64 |
| 6 | 0.125 | 0.5 | 2 | 0.5 | 2 | 0.25 | 2 | 2 | 1 | >64 | >64 |
| 7 | ≤.06 | ≤.06 | 1 | ≤.06 | 1 | ≤.06 | ≤.06 | ≤.06 | ≤.06 | 64 | >64 |
| 8 | 2 | 2 | 8 | 8 | 2 | 1 | 2 | 1 | 2 | >64 | >64 |
| 9 | 0.25 | 0.5 | 1 | 1 | 2 | 0.5 | 0.5 | 1 | 1 | >64 | >64 |
| 10 | | | | | | | | | | | |

TABLE IV

ACTIVITY OF AMINO ACID DERIVATIVES*

| Example # | Resistant | Sensitive | SA 446 | SA 489 | SA 447 | SA X400 | SA X778 | SA 491 | SA S13E | SA 1199 |
|---|---|---|---|---|---|---|---|---|---|---|
| 11 | 45 | 1.7 | 1 | 2 | 1 | 1 | 0.5 | 2 | 1 | 1 |
| 12 | 2.8 | 0.19 | 2 | 2 | 0.5 | 1 | 0.25 | 0.5 | 2 | 1 |
| 13 | 2.4 | 0.095 | 1 | 0.5 | 1 | 0.5 | 1 | 1 | 0.5 | 1 |
| 14 | >128 | 6.1 | | | | | | | | |
| 15 | 27 | 1.2 | 1 | 1 | 1 | 1 | 0.5 | 1 | 1 | 2 |
| 16 | >128 | 7 | | | | | | | | |
| 17 | >32 | 0.5 | 0.5 | 0.06 | 0.5 | 0.06 | 0.06 | 0.125 | 0.25 | 0.25 |
| 18 | 27 | 0.87 | 0.5 | 0.125 | 0.5 | 0.25 | 0.25 | ≦.06 | 0.5 | 0.5 |
| 19 | 64 | 2.6 | 2 | 1 | 2 | 2 | 2 | 1 | 2 | 2 |
| 20 | >128 | 2 | 0.5 | ≦.06 | 0.25 | ≦.06 | 0.25 | ≦.06 | 0.125 | 0.125 |
| 21 | 11 | 1.5 | 0.5 | 0.25 | 0.5 | 0.5 | 0.5 | 0.5 | 0.5 | 0.5 |

| Example # | SA 1199A | SH 105 | SH 415 | SE 270 | EF 180 | EF 180-1 | EF 2041 | EF 276 | EG 245 | HFRD | EC 14 |
|---|---|---|---|---|---|---|---|---|---|---|---|
| 11 | 1 | 0.5 | 1 | 0.5 | 8 | 0.25 | 1 | 2 | 1 | >64 | >64 |
| 12 | 0.25 | 0.125 | 0.25 | 0.125 | 1 | ≦.06 | 0.25 | 1 | 0.25 | 32 | >64 |
| 13 | 0.25 | 1 | 0.5 | 0.25 | 0.25 | ≦.06 | ≦.06 | 0.5 | ≦.06 | 16 | >64 |
| 14 | | | | | | | | | | | |
| 15 | 0.125 | 1 | 1 | 0.25 | 8 | ≦.06 | 0.25 | 0.5 | 1 | >64 | >64 |
| 16 | | | | | | | | | | | |
| 17 | ≦.06 | 0.5 | 1 | 0.25 | 1 | ≦.06 | ≦.06 | 0.06 | 0.06 | 32 | >64 |
| 18 | no growth | 1 | 1 | 0.25 | 2 | 0.5 | ≦.06 | 0.5 | 1 | 16 | >64 |
| 19 | no growth | 4 | 4 | 2 | 8 | 1 | 0.5 | 2 | 2 | >64 | >64 |
| 20 | no growth | 8 | 16 | 0.125 | 16 | 0.25 | ≦.06 | 0.125 | 0.5 | 8 | >64 |
| 21 | no growth | 2 | 2 | 0.5 | 1 | 0.5 | 0.5 | 1 | 1 | 2 | >64 |

| Example # | Resistant | Sensitive | SA 446 | SA 489 | SA 447 | SA X400 | SA X778 | SA 491 | SA S13E | SA 1199 |
|---|---|---|---|---|---|---|---|---|---|---|
| 22 | 6.7 | 0.66 | 1 | 1 | 1 | 0.5 | 1 | 0.5 | 2 | 2 |
| 23 | 2 | 0.29 | 1 | 0.5 | 1 | 2 | 2 | 0.5 | 2 | 0.5 |
| 24 | >128 | 4 | 4 | 2 | 4 | 2 | 1 | 1 | 2 | 2 |
| 25 | 27 | 1.3 | 4 | 1 | 2 | 2 | 2 | 2 | 2 | 1 |
| 26 | 23 | 0.76 | 2 | 0.5 | 1 | 0.5 | 0.5 | ≦.06 | 1 | 1 |
| 27 | 16 | 1 | 2 | 4 | 1 | 2 | 1 | 1 | 2 | 1 |
| 28 | 13 | 1.7 | 4 | 1 | 2 | 2 | 1 | 2 | 2 | 2 |
| 29 | 27 | 1.2 | 2 | 0.25 | 0.5 | 0.25 | 0.125 | ≦.06 | 0.5 | 0.125 |
| 30 | 38 | 2.3 | 8 | 1 | 2 | 2 | 1 | 2 | 2 | 2 |
| 31 | 5.6 | 0.33 | 0.5 | 2 | 2 | 2 | 0.5 | 0.5 | 1 | 0.5 |

| Example # | SA 1199A | SH 105 | SH 415 | SE 270 | EF 180 | EF 180-1 | EF 2041 | EF 276 | EG 245 | HFRD | EC 14 |
|---|---|---|---|---|---|---|---|---|---|---|---|
| 22 | 0.25 | 2 | 4 | 0.25 | 2 | ≦.06 | 1 | 1 | 0.25 | >64 | >64 |
| 23 | 0.25 | 1 | 1 | 0.125 | 0.5 | ≦.06 | 0.5 | 0.25 | 0.125 | >64 | >64 |
| 24 | 1 | 16 | 32 | 2 | >64 | 1 | 1 | 1 | 8 | >64 | >64 |
| 25 | 0.5 | 2 | 4 | 2 | 8 | ≦.06 | 1 | 2 | 2 | >64 | >64 |
| 26 | 0.125 | 1 | 2 | 0.25 | 4 | ≦.06 | 0.25 | 1 | 0.5 | >64 | >64 |
| 27 | 0.5 | 0.125 | 2 | 0.25 | 4 | 0.25 | 1 | 1 | 0.5 | 64 | >64 |
| 28 | 1 | 2 | 4 | 1 | 2 | 0.5 | 2 | 1 | 2 | >64 | >64 |
| 29 | ≦.06 | 0.125 | 0.5 | ≦.06 | 4 | ≦.06 | 0.125 | 0.25 | 2 | >64 | >64 |
| 30 | 1 | 2 | 2 | 1 | 8 | 0.5 | 1 | 2 | 2 | >64 | >64 |
| 31 | 0.25 | 0.5 | 2 | 0.5 | 1 | 0.25 | 1 | 2 | 0.5 | >64 | >64 |

| Example # | Resistant | Sensitive | SA 446 | SA 489 | SA 447 | SA X400 | SA X778 | SA 491 | SA S13E | SA 1199 |
|---|---|---|---|---|---|---|---|---|---|---|
| 32 | 16 | 0.76 | 1 | 1 | 1 | 2 | 0.5 | 0.125 | 0.25 | 0.25 |
| 33 | 27 | 2.6 | 1 | 2 | 1 | 1 | 1 | 0.5 | 1 | 0.5 |
| 34 | 38 | 0.44 | 0.125 | ≦.06 | 0.125 | ≦.06 | ≦.06 | ≦.06 | ≦.06 | 0.125 |
| 35 | 4.8 | 0.66 | 2 | 2 | 2 | 2 | 1 | 1 | 2 | 2 |
| 36 | >128 | 16 | 8 | 4 | 16 | 4 | 4 | 2 | 4 | 4 |
| 37 | >32 | 0.87 | 0.5 | 0.25 | 1 | 0.25 | 0.25 | 0.5 | 0.25 | 0.5 |
| 38 | 6.7 | 0.19 | 1 | 0.25 | 1 | 1 | 0.5 | ≦.06 | 0.5 | 1 |
| 39 | 45 | 0.38 | ≦.06 | ≦.06 | 0.5 | ≦.06 | ≦.06 | ≦.06 | 0.125 | 0.125 |
| 40 | >128 | 9.2 | 4 | 4 | 8 | 4 | 4 | 2 | 4 | 4 |
| 41 | >128 | 84 | 32 | 16 | 32 | 16 | 8 | 4 | 16 | 16 |
| 42 | 128 | 0.66 | 0.5 | 0.5 | 0.5 | 0.5 | 2 | 1 | 1 | |

TABLE IV-continued

ACTIVITY OF AMINO ACID DERIVATIVES*

| Example # | SA 1199A | SH 105 | SH 415 | SE 270 | EF 180 | EF 180-1 | EF 2041 | EF 276 | EG 245 | HFRD | EC 14 |
|---|---|---|---|---|---|---|---|---|---|---|---|
| 32 | ≤.06 | 0.125 | 0.5 | 0.125 | 2 | 0.125 | 1 | 2 | 0.5 | >64 | >64 |
| 33 | 0.25 | 0.5 | 0.5 | 0.25 | 4 | 0.5 | 2 | 4 | 1 | >64 | >64 |
| 34 | ≤.06 | ≤.06 | 4 | 0.25 | 2 | ≤.06 | 0.25 | ≤.06 | ≤.06 | 64 | >64 |
| 35 | 1 | 0.5 | 2 | 1 | 1 | 0.25 | 0.5 | 1 | 1 | >64 | >64 |
| 36 | 4 | 2 | >64 | 16 | >64 | 4 | 8 | 4 | 16 | >64 | >64 |
| 37 | 0.125 | 0.25 | 4 | 0.5 | >64 | 0.25 | 0.5 | 0.25 | 0.5 | 64 | >64 |
| 38 | ≤.06 | 1 | 1 | 1 | 2 | no growth | ≤.06 | 0.25 | 0.5 | no growth | >64 |
| 39 | ≤.06 | 0.5 | 2 | 0.25 | 2 | no growth | ≤.06 | ≤.06 | 0.5 | no growth | >64 |
| 40 | 2 | 4 | 64 | 4 | >64 | 4 | 2 | 1 | 16 | >64 | >64 |
| 41 | 8 | 16 | 64 | 8 | >64 | 4 | 8 | 8 | >64 | no growth | >64 |
| 42 |  | 0.5 | 1 | 1 | 64 |  |  |  |  |  | >64 |

| *Abbreviations | Organism |
|---|---|
| Resistant | Enterococcus faecium and faecalis (geometric mean of 4–6 isolates) |
| Sensitive | Enterococcus faecium and faecalis (geometric mean of 4–6 isolates) |
| SA 446 | Staphylococcus aureus 446 |
| SA 489 | Staphylococcus aureus 489 |
| SA 447 | Staphylococcus aureus 447 |
| SA X400 | Staphylococcus aureus X400 |
| SA X778 | Staphylococcus aureus X778 |
| SA 491 | Staphylococcus aureus 491 |
| SA S13E | Staphylococcus aureus S13E |
| SA 1199 | Staphylococcus aureus SA1199 |
| SA 1199A | Staphylococcus aureus SA1199A |
| SH 105 | Staphylococcus haemolyticus 105 |
| SH 415 | Staphylococcus haemolyticus 415 |
| SE 270 | Staphylococcus epidermidis 270 |
| EF 180 | Enterococcus faecium 180 |
| EF 180-1 | Enterococcus faecium 180-1 |
| EF 2041 | Enterococcus faecalis 2041 |
| EF 276 | Enterococcus faecalis 276 |
| EG 245 | Enterococcus gallinarum 245 |
| HFRD | Haemophilus influenzae RD |
| EC 14 | Escherichia coli EC14 |

We claim:
1. A compound of the formula

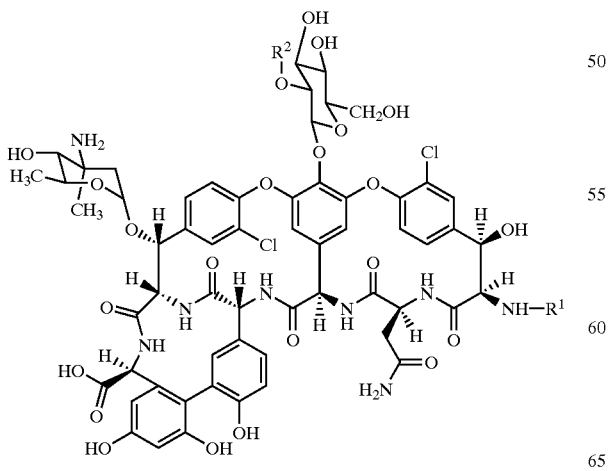

wherein $R^1$ represents $C_2$–$C_{10}$ alkanoyl which is substituted, or which is substituted by a phenyl group, or which is substituted at a position other than the carbon alpha- to the alkanoyl carbonyl group by an amino or protected amino group;

benzoyl or substituted benzoyl bearing one or two substituents each of which is independently halo, loweralkyl of $C_1$–$C_4$, loweralkoxy of $C_1$–$C_4$ or phenyl;

an α-amino acyl group wherein the α-carbon is substituted with the side chain of an amino acid in which a reactive group, when present, is optionally protected, wherein said α-amino acid is selected from the group consisting of:

alanine,
arginine,
asparagine,
aspartic acid,
cysteine,
glutamic acid,
glutamine,
glycine,
histidine,
isoleucine,
leucine,
lysine,
methionine,
3-phenylalanine,
3-(p-chlorophenyl)alanine,
proline,
serine,
threonine,
tryptophan and valine, in either D- or L-form; or an α-amino acyl group as defined above which bears on the amine a substituent which is alkyl of $C_1$–$C_{10}$, benzyl, phenylbenzyl, or p-chlorobenzyl, with the proviso that N-methyl-D-leucine, N-ethyl-D-leucine and derivatives thereof are excluded as an amino acids;

$R^2$ represents hydrogen or an epivancosaminyl of the formula

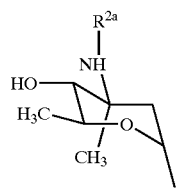

wherein $R^{2a}$ represents hydrogen or —CH$_2$—R$^3$; and R$^3$ represents
hydrogen,
C$_1$–C$_{11}$alkyl,
C$_1$–C$_{11}$ alkyl-R$^4$, or
R$^4$-(linker$_m$-R$^4$)$_p$,
wherein m is an integer of 0 or 1; p is an integer of 0 or 1, and each R$^4$ is independently phenyl or phenyl substituted by one or two substituents, each of which is independently halo, loweralkyl of C$_1$–C$_8$, loweralkoxy of C$_1$–C$_8$, loweralkylthio of C$_1$–C$_4$, or trifluoromethyl, and "linker" is —O—, —CH$_2$—, or —O—(CH$_2$)$_n$— wherein n is 1–3.

2. A compound of claim 1 in which R$^2$ is an epivancosaminyl group wherein R$^{2a}$ represents hydrogen.

3. A compound of claim 2 in which R$^2$ is an epivancosaminyl group wherein R$^{2a}$ represents —CH$_2$—R$^3$.

4. A compound of claim 3 in which R$^3$ is p-biphenylyl.

5. A compound of claim 3 in which R$^3$ is p-(p-chlorophenyl)phenyl.

6. A composition comprising a compound of claim 1 in combination with a pharmaceutically-acceptable diluent or carrier.

7. The compound of claim 1, wherein R$^1$ represents
C$_2$–C$_{10}$ alkanoyl which is unsubstituted, or which is substituted by a phenyl group, or which is substituted at a position other than the carbon alpha- to the alkanoyl carbonyl group by an amino or protected amino group; or benzoyl or substituted benzoyl bearing one or two substituents each of which is independently halo, loweralkyl of C$_1$–C$_4$, loweralkoxy of C$_1$–C$_4$ or phenyl.

8. A process for the preparation of a compound as claimed in any one of claims 1–5 which comprises reacting a parent glycopeptide of the formula

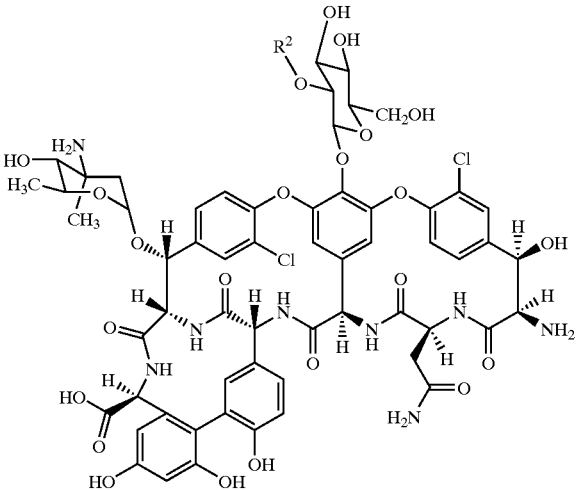

wherein R$^2$ is as defined in claim 1, with an activated ester of an alkanoic acid of the desired R$^1$ as defined in claim 1, and optionally, thereafter reductively alkylating the N$^{DISACC}$ amine and/or forming a pharmaceutically acceptable salt.

* * * * *